(12) United States Patent
Gokaraju et al.

(10) Patent No.: US 11,903,991 B2
(45) Date of Patent: Feb. 20, 2024

(54) SYNERGISTIC DIETARY SUPPLEMENT COMPOSITIONS FOR THE PREVENTION, TREATMENT OR CONTROL OF INFLAMMATORY DISORDERS

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakati, Vijayawada (IN); Kiran Bhupathiraju, Vijayawada (IN); Venkata Krishna Raju Alluri, Vijayawada (IN); Krishanu Sengupta, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 537 days.

(21) Appl. No.: 17/201,865

(22) Filed: Mar. 15, 2021

(65) Prior Publication Data

US 2021/0205401 A1 Jul. 8, 2021

Related U.S. Application Data

(60) Division of application No. 15/229,710, filed on Aug. 5, 2016, now Pat. No. 10,953,067, which is a continuation-in-part of application No. PCT/IN2015/000065, filed on Feb. 2, 2015.

(30) Foreign Application Priority Data

Feb. 5, 2014 (IN) .............................. 531/CHE/2014

(51) Int. Cl.
*A61K 36/00* (2006.01)
*A61K 36/9066* (2006.01)
*A61K 36/185* (2006.01)
*A61K 36/324* (2006.01)
*A61K 45/06* (2006.01)

(52) U.S. Cl.
CPC ........ *A61K 36/9066* (2013.01); *A61K 36/185* (2013.01); *A61K 36/324* (2013.01); *A61K 45/06* (2013.01); *A61K 2236/15* (2013.01); *A61K 2236/31* (2013.01); *A61K 2236/33* (2013.01); *A61K 2236/331* (2013.01); *A61K 2236/35* (2013.01); *A61K 2236/39* (2013.01); *A61K 2236/51* (2013.01); *A61K 2236/55* (2013.01)

(58) Field of Classification Search
None
See application file for complete search history.

(56) References Cited

U.S. PATENT DOCUMENTS

| | | | |
|---|---|---|---|
| 5,629,351 A | 5/1997 | Taneja et al. |
| 5,888,514 A | 3/1999 | Weisman |
| 7,338,674 B2 | 3/2008 | Palpu et al. |
| 7,658,957 B2 | 2/2010 | Palpu et al. |
| 2004/0086581 A1 | 5/2004 | Jones |
| 2008/0166432 A1 | 7/2008 | Patell et al. |
| 2012/0301432 A1 | 11/2012 | Gokaraju |

FOREIGN PATENT DOCUMENTS

| | | |
|---|---|---|
| JP | 09227398 A | 9/1997 |
| WO | WO 2006/061675 A1 | 6/2006 |
| WO | WO 2008/036932 A2 | 3/2008 |
| WO | WO 2010/029578 A2 | 3/2010 |
| WO | WO 2010/119294 A2 | 10/2010 |
| WO | 2011099029 A1 | 8/2011 |
| WO | WO 2011/125070 A2 | 10/2011 |

OTHER PUBLICATIONS

Cuaz-Perolin, et al., "Antiinflammatory and Antiatherogenic Effects of the NG-kB Inhibitor Acetyl011-Keto-beta-Boswellic Acid in LPS-Challenged ApoE-/-Mice", Arterioscler Thromb Vasc Biol Feb. 2008, pp. 272-277.
Gupta, et al., "Effects of Boswellia Serrata Gum Resin in Patents with Bronchial Asthma: Results of a Double-Blind, Placebo Controlled, 6-Week Clinical Study", Eur. J. Med. Res. (1998) 511-514.
Gupta, et al., "Effects of Gum Resin of Boswellia serrata in Patients with Chronic Colitis", Planta Med 67 (2001) 391-395.
Hermann, et al., "Pharmacology of Curcuma longa", Planta Med. 57 (1991) pp. 1-7.
Kelloff, et al., "Strategy and Planning for Chemopreventive Drug Development: Clinical Development Plans II", Journal of Cellular Biochemistry 265:55-71 (1996).
Kimmatkar, et al., "Efficacy and tolerability of Boswellia serrata exract in treatment of osteoarthritis of knee—A randomized double blind placebo controlled trial", Phytomedicine 10:3-7 (2003).
Moussaieff, et al., "Incensole Acetate, a Novel Anti-Inflammatory Compound Isolated from Boswellia Resin, Inhibits Nuclear Factor-kB Activation", Molecular Pharmacology, vol. 72, No. 6 (1657-1664) 2007.
Pungle, et al., "Immunomodulatory activity of boswellic acids of Boswellia serrata Roxb.", Indian Journal of Experimental Biology, vol. 41, Dec. 2003, pp. 1460-1462.
Author Therayar Title of the Publication Kadukaai Kudineer Page(S) being Submitted 06) p. 01-06) (Ref. p. of publication p. 55-57) Publication Date 1979 Publisher Therayar Sekarappa Publisher: C.C.R.A.S, Place of Publication New Delhi.†

(Continued)

*Primary Examiner* — Russell G Fiebig
(74) *Attorney, Agent, or Firm* — Kramer & Amado, P.C.

(57) ABSTRACT

A method for treating an inflammation, arthritis, or a joint disease in a patient in need thereof, comprising administering to the patient an herbal composition, where the herbal composition includes a therapeutically effective amount of an extract of *Terminalia chebula*; a therapeutically effective amount of an extract of *Curcuma longa*; and a therapeutically effective amount of a non-acidic, water-immiscible organic solvent extract of a *Boswellia serrata* resin.

16 Claims, No Drawings

(56) References Cited

OTHER PUBLICATIONS

Author Krsnarama Bhatta Title of the Publication Siddhabhesajamanimala (Mahisi Mutra Yoga) Page(S) being Submitted 07 (p. 01-07) (Ref. p. of publication p. 242) Publication Date 2003 Publisher Commentary by Kaladhara Bhatta, Chaukhambha Krishnadas Academy Place of Publication Varanasi.†

Author Mohammad Akmal Khan Title of the Publication Qaraabaadeen Azam wa Akmal, ( Nuskha-e-Qatoor) Page(S) being Submitted 03 (p. 01-03) (Ref. p. of publication p. 589) Publication Date 1897AD Publisher Matba Siddiqi/ Matba Mustafai Place of Publication Delhi.†

† cited by third party

SYNERGISTIC DIETARY SUPPLEMENT COMPOSITIONS FOR THE PREVENTION, TREATMENT OR CONTROL OF INFLAMMATORY DISORDERS

CROSS-REFERENCE TO RELATED APPLICATIONS

This application is a divisional of parent U.S. application Ser. No. 15/229,710 filed on Aug. 5, 2016, which is a continuation-in-part of parent International Patent Application No. PCT/IN2015/000065, filed on Feb. 2, 2015, now published as WO/2015/118557, which claims priority to Indian Application No. 531/CHE/2014, dated Feb. 5, 2014. The entire disclosure of each prior application is incorporated by reference herein in its entirety.

TECHNICAL FIELD OF THE INVENTION

The invention relates to synergistic compositions for the treatment of Inflammation and Arthritis. The composition comprises a therapeutically effective combination of extracts or fractions derived from the medicinal herbs such as *Terminalia chebula, Curcuma longa* in combination with *Boswellia serrata* non-acidic resin extracts (BNRE) derived from *Boswellia serrata*. The synergistic compositions may further contain pharmaceutically or nutraceutically acceptable actives, excipients, carriers or diluents. The invention further relates to the methods of use of the composition for the treatment of disease conditions related to inflammation, which include arthritis, osteoarthritis and joint pain.

BACKGROUND OF THE INVENTION

*Terminalia chebula* is a gentle purgative, astringent (unripe fruits are more purgative, ripe ones are more astringent), stomachic, antibilious, alcerative. It is used in prescriptions for treating flatulence, constipation, diarrhea, dysentery, cyst, digestive disorders, vomiting, enlarged liver and spleen, cough and bronchial asthma, and for metabolic harmony. Bark is used as diuretic. The Ayurvedic Pharmacopoeia of India, along with other therapeutic applications, indicated the use of powder of mature fruits in intermittent fevers, chronic fevers, anaemia and polyuria. The fruits of *T. chebula* are used in combination with *Emblica officinalis* and *T. bellerica* (under the name Triphalaa) in the treatment of liver and kidney dysfunctions. The main purgative ingredient of Triphalaa is *T. chebula*. Shikimic, gallic, triacontanoic and palmitic acids, beta-sitosterol, daucosterol, triethyl ester of chebulic acid and ethyl ester of gallic acid; a new ellagitannin, terchebulin, along with punicalagin and teaflavin A have been isolated from the fruits of *T. chebula*. A new triterpene, chebupentol, and arjungenin, terminoic acid and arjunolic acid were also isolated from the fruit.

The PCT Publication WO2010119294 provides a composition for oral administration comprising as active ingredient a combination of material derived from the plants *Andrographis paniculata, Tinospora cordifolia, Eclipta alba, Tephrosia purpurea, Vitex negundo, Zinziber officinale, Terminalia chebula* and *Withania somnifera*. Methods for preparing such a composition and the use of such a composition in therapy of animals are also provided. The composition is used for treating e.g. arthritis, respiratory infection in animals.

The granted U.S. Pat. Nos. 7,658,957 and 7,338,674 and PCT Publication No. WO06061675 provide a novel herbal composition for treatment of arthritis and inflammation. The herbal composition comprises a therapeutically effective combination of extracts obtained from the plants *Terminalia chebula, Pluchea lanceolata, Desmodium gangeticum, Vitex negunto* and *Zingiber officinale*, optionally along with pharmaceutically acceptable additives. The invention further comprises methods of making the herbal composition and methods of use for the treatment of arthritis and inflammation.

The U.S. Publication No. US20080166432 relates to extracts from *Terminalia* plant species that are capable of being used in methods for managing diseases such as cardiovascular disease, diabetes, degenerative neurological diseases, cancer, age related diseases like amyloidosis, acute pancreatitis, arthritis, atherosclerosis, cancer, heart diseases, inflammatory bowel disease, myocardial infarction, senile dementia, retinal degeneration and senile cataract; owing to the extracts anti oxidation potential. The US'432 also relates to extracts from *Terminalia* plant species that are capable of being used in methods for managing various infectious diseases.

Turmeric, the powdered rhizome of the herb *Curcuma longa* L. (Zingiberaceae), has been used extensively in Indian and Asian cuisine and it is also used as a coloring and flavoring agent. Powdered turmeric, or its extract, is found in numerous commercially available botanical supplements. In Ayurvedic medicine, turmeric has traditionally been used to treat inflammation, skin wounds and tumors (Ammon and Wahl, 1991, Planta Med., 57:1-7). Turmeric extracts have been reported to have anti-microbial, anti-inflammatory, antioxidant and anticancer effects. In preclinical animal studies turmeric has shown anti-inflammatory, cancer chemopreventive and anti-neoplastic properties (Kelloff et al., 1996, J. Cell. Biochem. Supplement 26:54-71). The best characterized of the compounds found in turmeric are curcuminoids, which have been shown to reduce inflammation.

The U.S. Publication No. US20040086581 relates to a joint and arthritis pain formula and more particularly to a composition to promote healing and relieve arthritis symptoms. The composition comprises a therapeutically effective combination of CMO-Cetyl Myristoleate; MSM-Organic Sulphur; Collagen; Glucosamine; OPC Proanthocyandians; Bromelain *Boswellia*; Turmeric; Feverfew; Ginger; White willow extract; Manganese Chelate; Sweetener; Maltodextrin; Buffered Vitamin C.

The PCT publication WO2011125070 relates to oral supplementation of curcuminoid with essential oil of turmeric to enhance the bio availability of curcumin for the prophylaxis, treatment, maintenance therapy and as add-on therapy for disease conditions such as cancer, heart diseases, diabetes, rheumatoid arthritis, osteoarthritis, Alzheimer's disease, inflammatory bowel diseases.

The gum resin of the plant *Boswellia serrata* (Burseraceae) has long been in use for the treatment of rheumatoid arthritis and gout by the practitioners of Ayurvedic medicines in the Indian system of medicine. Various extracts of the gum resin have shown potent anti-inflammatory and anti-atherogenic activity in laboratory animals [Cuaz-Pérolin et al., Arterioscler Thromb Vasc Biol February 2008]. Incensole acetate, a *Boswellia* compound isolated was proved to be a NF-kappa B inhibitor and useful as anti-inflammatory compound [Moussaieff et al., Mol Pharmacol 72, 1657-1664, 2007]. The ethanolic extract of the gum resin of *B. serrata* inhibits the formation of Leukotriene B4 in rat peritoneal neutrophils. Leukotriene B4 is one of the important mediators of inflammatory reactions [Ammon, H. P. T. et al., Planta *Medica*, 57, 203 (1991)]. The extract of *Boswellia* was found to be a potent anti-arthritic agent

[Kimmatkar et al; Phytomedicine. 2003 January; 10(1):3-7.], and immune-modulatory agent [Pungle et al; Indian J Exp Biol. 2003 December; 41(12):1460-1462]. The cholesterol lowering action of *Boswellia serrata* was also proved [Zutshi U et al, Indian J Pharmac. 18, 182-183, 1986]. In fact, a randomized, double blind, placebo controlled, cross-over clinical trial with *Boswellia* extract on a group of patients with osteoarthritis of knee exhibited statistically significant mean improvements with respect to reduction in pain, decreased swelling and increased knee flexion [Kimmatkar N, et. al., Phytomedicine 2003; 10: 3-7]. The efficacy of *Boswellia* extracts against chronic colitis [Gupta I, et. al., Planta Med. 2001; 67: 391-395], Crohn's disease [Gerhardt H, et. al., Z Gastroenterol 2001; 39: 11-17] and bronchial asthma [Gupta I, et. al., Eur J Med Res 1998; 3: 511-51] was also reported.

Many different extracts of *Boswellia* gum resin have been prepared and most prominent of them are *Boswellia serrata* acidic extract, *Boswellia serrata* non acidic extract and water soluble extract containing polysaccharides.

The U.S. Pat. No. 5,629,351 relates to a novel fraction comprising a mixture of boswellic acids, wherein the fraction exhibits anti-inflammatory and anti ulcerogenic activities and a process for isolating a boswellic acid fraction and individual boswellic acids therefrom.

The PCT Patent Publication WO08036932 provides a method for making compositions derived from *Boswellia* species (frankincense or olibanum) having uniquely elevated volatile oil, boswellic acids, and polysaccharide compounds, particularly, human oral delivery formulations, and methods for use of such compositions, e.g. for treating/preventing arthritis, inflammatory disorders, osteoarthritis, rheumatoid diseases and low back pain.

The U.S. Pat. No. 5,888,514 refers to a composition for treating a mammal having a condition characterized by bone or joint inflammation where extract of *Boswellia serrata* is used as one of the ingredients.

The U.S. Publication No. US2012301432 provides *Boswellia* low polar gum resin extract (BLPRE) comprising a novel phytochemical composition alone and its compositions for the prevention, control and treatment of disorders such as diabetes, obesity, metabolic syndrome, excess body weight, inflammation, asthma, Alzheimer's, cognitive disorders, neurological disorders, cartilage degradation, aging, skin disorders, hypertriglyceridemia, hyperlipidemia, hypercholesterolemia, cholesterol disorders, hypertension, high blood pressure, immune disorders, cancer, coronary heart disease, infectious diseases, osteoporosis, osteoarthritis, rheumatoid arthritis, joint pain, joint discomfort and several other conditions associated thereof.

The PCT Publication No. WO201029578 discloses synergistic nutraceutical anti-inflammatory compositions comprising therapeutically effective combination of an extract selectively enriched in 3-O-acetyl-11-keto-β-boswellic acid (AKBA) derived from *Boswellia serrata* and *Boswellia serrata* non-acidic resin extract (BNRE). The compositions can be used to prevent, control and treat inflammation and several inflammatory related diseases including asthma, osteoarthritis, rheumatoid arthritis, endothelial dysfunction and the like. The invention further discloses the amelioration of pro-inflammatory biomarker proteins or molecules, whose expression/production is altered during inflammatory diseases.

Inflammation is a complex pathophysiological process mediated by a variety of signaling molecules produced by leucocytes, macrophages and mast cells as well as by the activation of complement factors that bring about edema formation as a result of extravasations of fluid and proteins and accumulation of leucocytes at the inflammatory site. Arthritis is a disease affecting the musculoskeletal system, particularly the joints. Inflammation is a common clinical conditions and rheumatoid arthritis (RA) is a chronic debilitating autoimmune disorder that affects about 3 million Indians and 50 million Americans etc. Osteoarthritis is the most common joint degenerative disorder sets in as a result of aging, wear and tear on a joint.

Accordingly, there is a real and continuing need in the art for safe and cost-effective medicines for treating inflammation and arthritis. Hence the aim of present invention is to develop synergistic compositions, specifically those containing the herbal extracts and/or bioactive fractions to treat the Inflammation and Arthritis without the undesired side effects. In particular, the invention provides compositions comprising extracts or fractions derived from *Terminalia chebula*, *Curcuma longa* and *Boswellia serrata*.

There is however no prior art, to the best of inventors' knowledge, relating to the compositions comprising extracts derived from *Terminalia chebula* and *Curcuma longa* in combination with *Boswellia serrata* non-acidic resin extracts (BNRE) for the prevention, control and treatment of inflammatory conditions and joint disorders.

Therefore, the main object of the present invention is to provide synergistic nutraceutical or dietary supplement compositions comprising therapeutically effective combination of extracts or fractions from *Terminalia chebula*, *Curcuma longa* and *Boswellia serrata* non-acidic resin extract (BNRE), optionally containing other natural ingredients.

SUMMARY OF THE INVENTION

In accordance with the above object, the invention discloses synergistic compositions for the prevention, control or treatment of inflammation and/or disease conditions associated with or related to inflammation including asthma, atherosclerosis, endothelial dysfunction, osteoarthritis, rheumatoid arthritis and the like.

In another aspect, the invention provides synergistic compositions comprising therapeutically effective combination of extracts or fractions from *Terminalia chebula*, *Curcuma longa* and *Boswellia serrata* non-acidic resin extract (BNRE) for the prevention, control and treatment of one or more components of other inflammatory diseases including arthritis or rheumatoid arthritis. Non-limiting examples of arthritis include rheumatoid (such as soft-tissue rheumatism and non-articular rheumatism, fibromyalgia, fibrositis, muscular rheumatism, myofascial pain, humeral epicondylitis, frozen shoulder, Tietze's syndrome, fascitis, tendinitis, tenosynovitis, bursitis), juvenile chronic, joint disorders, spondyloarthropathies (ankylosing spondylitis), osteoarthritis, hyperuricemia and arthritis associated with acute gout, chronic gout and systemic lupus erythematosus and degenerative arthritis.

In yet further aspect, the present invention provides synergistic compositions for the amelioration of the expression and/or production of biomolecules or biomarkers associated with inflammation and/or disease conditions associated with inflammation, osteoarthritis, rheumatoid arthritis, cartilage degradation, which include but not limited to 5-lipoxygenase (5-LOX), 5-Lipoxygenase activating protein (FLAP), macrophage/adipocyte fatty acid-binding protein-2 (aP2/FABP), interferon-gamma (IFN-γ), interleukin-4 (IL-4), intercellular cell adhesion molecule (ICAM)-1, vascular cell adhesion molecule (VCAM)-1, Matrix metalloproteinase (MMP)-3, TNF-α and IL-1β in mammals.

Various embodiments disclosed herein relate to a herbal composition, comprising:
- a therapeutically effective amount of an extract of *Terminalia chebula*;
- a therapeutically effective amount of an extract of *Curcuma longa*; and
- a therapeutically effective amount of a non-acidic, water-immiscible organic solvent extract of a *Boswellia serrata* resin.

In various embodiments, the non-acidic, water-immiscible organic solvent extract of the *Boswellia serrata* resin is obtained by:
- extracting *Boswellia serrata* gum resin with a water-immiscible organic solvent to obtain an organic solution;
- extracting the organic solution with aqueous alkali to remove boswellic acids from the organic solution; and
- removing the water-immiscible organic solvent from the organic solution to obtain an organic solvent extract. In some embodiments, the method of obtaining the non-acidic, water-immiscible organic solvent extract of the *Boswellia serrata* resin further comprises a step of removing volatile components from the organic solvent extract under vacuum to obtain the desired non-acidic, water-immiscible organic solvent extract.

In some embodiments, the composition further comprises a plant derived anti-inflammatory agent, a pharmaceutically, nutraceutically, or dietetically acceptable carriers, a pharmaceutically, nutraceutically, or dietetically acceptable excipient, or a mixture thereof.

In some embodiments, the composition comprises an extract of *Terminalia chebula* prepared from dried fruits of *Terminalia chebula*; an extract of *Curcuma longa* prepared from dried rhizomes of *Curcuma longa*; and a non-acidic, water-immiscible organic solvent extract of a *Boswellia serrata* resin prepared from the gum resin of *Boswellia serrata*.

According to various embodiments disclosed herein, the composition comprises from 20% by weight to 75% by weight of the extract of *Terminalia chebula*. The composition may comprise from 10% by weight to 40% by weight, or from 15% by weight to 40% by weight, of the extract of *Curcuma longa*. The composition may comprise from 10% by weight to 40% by weight of the non-acidic, water-immiscible organic solvent extract of the *Boswellia serrata* resin. The composition may further comprise from 0% by weight to 20% by weight of a *Boswellia serrata* extract which contains at least 5% 3-O-acetyl-11-keto-β-boswellic acid (AKBA). The above percentages are based on the total weight of the *Terminalia chebula, Curcuma longa,* and *Boswellia serrata* extracts.

In some embodiments, the composition comprises from 25% by weight to 65% by weight, or from 25% by weight to 45% by weight, of the extract of *Terminalia chebula*. The composition may comprise from 12% by weight to 30% by weight, or from 15% by weight to 25% by weight, of the extract of *Curcuma longa*. The composition may comprise from 12% by weight to 30% by weight, or from 15% by weight to 25% by weight, of the non-acidic, water-immiscible organic solvent extract of the *Boswellia serrata* resin. The composition may further comprise from 15% by weight to 25% by weight of a *Boswellia serrata* extract which contains at least 5% 3-O-acetyl-11-keto-β-boswellic acid (AKBA). The above percentages are based on the total weight of the composition.

DETAILED DESCRIPTION OF THE INVENTION

The invention will now be described in detail in connection with certain preferred and optional embodiments, so that various aspects thereof may be more fully understood and appreciated.

Source of the Plant Material:

The herbs *Terminalia chebula, Curcuma longa* and *Boswellia serrata* used in the present invention are collected from Eastern India, Andhra Pradesh and Madhya Pradesh respectively.

Inflammation is a response of the vascular tissues to stimuli such as pathogens, damaged cells or allergic agents, which enter into the body. It is a protective mechanism by the organism to remove harmful pathogens or agents and protect the tissues. Pro-inflammatory cytokines such as TNFα, IL-1β, IL-6, GM-CSF and CD4+, Th2 subset derived IL-4, IL-5 and IL-13 lymphokines are considered as the key factors of immune pathogenesis of inflammatory diseases [Knight D A, et. al., J. Allergy Clin. Immunol. 2001; 108: 797-803]. 5-Lipoxygenase is an enzyme critical for leukotriene synthesis from arachidonic acid, a key step in the inflammatory process. Leukotrienes are key mediators of inflammatory diseases.

The inventors have prepared several plant extracts and tested them for anti-oxidant activity using Reactive Oxygen Species (ROS) scavenging assay; and anti-inflammatory activities (5-Lipoxygennase inhibition and inhibition of cytokines in cellular models) for identifying active extracts. Several plant extracts including *Terminalia chebula* fruit extract, *Curcuma longa* root extract, *Boswellia serrata* non-acidic gum resin extract and *Boswellia serrata* gum acidic resin extract showed promising activity during the screening. The inventors have randomly prepared and tested several compositions comprising the extracts of *Terminalia chebula* fruit in combination with several plant extracts in an effort to find a composition that can show better efficacy in ameliorating the inflammatory processes and in expression or production of key biomarker molecules associated with inflammatory disorders, and to identify a better agent for controlling, treating and preventing inflammatory disease conditions. Several enzyme based and cell based in-vitro anti-inflammatory studies were conducted on a broad array of compositions containing *Terminalia chebula* in combination with several plant extracts. It was found surprisingly found that compositions comprising extract(s) or fractions or enriched fraction(s) or compound(s) derived from *Terminalia chebula* in combination with extracts or enriched fractions or compounds derived from *Curcuma longa* and *Boswellia serrata* non-acidic resin extract (BNRE) potently inhibited the 5-lipoxygenase enzyme (5-LOX) activity. The water extract of *Terminalia chebula* fruit, methanol extract of *Curcuma longa* and *Boswellia serrata* non-acidic resin extract (BNRE) a non-acidic gum resin extract obtained after removing/separating the acidic compounds and volatile compounds from the water immiscible organic solvent extract of *Boswellia serrata* gum resin, such as Methyl isobutyl ketone were used to demonstrate the invention. However, extracts obtained using other solvents such as dichloromethane, dichloroethane, ethanol, methanol; water and mixtures thereof; ethyl acetate; C1 to C7 hydrocarbons; hydroalchohol and mixtures can also be used to inhibit the 5-lipoxygenase enzyme (5-LOX) activity.

The individual extracts and the compositions were tested for their efficacy to inhibit 5-lipoxygenase enzyme (5-LOX) activity in an enzyme based assay. The individual extracts and compositions were also tested for their efficacy to inhibit productions of a few key pro-inflammatory cytokines/chemokines such as IL-1β, TNF-α and MMP-3 in in vitro cellular models. It was found very surprisingly that compositions comprising therapeutically effective combination of extracts or fractions from *Terminalia chebula* and *Curcuma longa*, and *Boswellia serrata* non-acidic resin extract (BNRE) showed synergistic inhibition of 5-LOX activity.

The individual extracts and the compositions comprising therapeutically effective combination of extracts or fractions from *Terminalia chebula* and *Curcuma longa*, *Boswellia serrata* non-acidic resin extract (BNRE) and *Boswellia serrata* extract standardized to 75%-85% total acids by volumetric assay which contain at least 5% 3-O-acetyl-11-keto-β-boswellic acid (AKBA) were tested for their efficacy to inhibit 5-lipoxygenase enzyme (5-LOX) activity, and production of key pro-inflammatory cytokines/chemokines such as IL-1β, TNF-α and MMP-3. It was found very surprisingly that compositions comprising therapeutically effective combination of extracts or fractions from *Terminalia chebula* and *Curcuma longa*, *Boswellia serrata* non-acidic resin extract (BNRE) and *Boswellia serrata* extract standardized to 75%-85% total acids by volumetric assay which contain at least 5% 3-O-acetyl-11-keto-β-boswellic acid (AKBA) showed synergistic inhibition of 5-LOX activity and the cytokines/chemokines production.

In a preferred embodiment, the present invention provides synergistic anti-inflammatory compositions comprising therapeutically effective combination of extracts or fractions derived from *Terminalia chebula* and *Curcuma longa*, and non-acidic resin extract (BNRE) derived from *Boswellia serrata*.

In other important embodiment, the compositions comprising therapeutically effective combination of extracts or fractions derived from *Terminalia chebula* and *Curcuma longa*, and non-acidic resin extract (BNRE) derived from *Boswellia serrata* can be used to prevent or cure or treat inflammation and/or one or more disease conditions related to or associated with inflammation.

In another aspect, the present invention provides synergistic anti-inflammatory compositions obtained by combining *Terminalia chebula* and *Curcuma longa* derived extracts or fractions and *Boswellia serrata* non-acidic resin extract (BNRE) at certain specific ratio to obtain a better effect than that obtained when the extracts or fractions were given individually, i.e. synergistic amelioration of inflammatory processes and/or expression or production of pro-inflammatory biomolecules/protein markers.

In another preferred embodiment, the synergistic anti-inflammatory compositions comprising therapeutically effective combination of extracts or fractions derived from *Terminalia chebula* and *Curcuma longa*, and *Boswellia serrata* non-acidic resin extract (BNRE) optionally contain *Boswellia serrata* acidic extract standardized to one or more boswellic acid compounds.

In yet another preferred embodiment, the present invention provides a synergistic composition consisting of *Terminalia chebula* extract or fraction in the range from 20% to 75% by weight, *Curcuma longa* extract or fraction in the range from 10% to 40% by weight and *Boswellia serrata* non-acidic resin extracts (BNRE) in the range from 10% to 40% by weight.

In a further aspect, the invention provides synergistic compositions containing extracts or fractions derived from *Terminalia chebula* and *Curcuma longa* and *Boswellia serrata* non-acidic resin extract (BNRE) for the amelioration of the expression or production of the biomolecules/biomarkers/certain redox-sensitive pro-inflammatory genes related to or associated with inflammation which include but not limited to 5-lipoxygenase (5-LOX), 5-Lipoxygenase activating protein (FLAP), macrophage/adipocyte fatty acid-binding protein (aP2/FABP), IFN-γ, IL-4, ICAM-1, VCAM-1, Matrix metalloproteinases (MMPs) such MMP-13, MMP-3 and MMP-1, NFκB TNF-α and IL-1β, IL-13, IL-6, IL-2, in mammals in need thereof.

In yet another aspect, the invention provides synergistic compositions containing extracts or fractions derived from *Terminalia chebula* and *Curcuma longa* and *Boswellia serrata* non-acidic resin extract (BNRE) for the prevention, control and treatment of one or more disease conditions related to or associated with inflammation which include but not limited to asthma, arthritis, osteoarthritis, rheumatoid arthritis, atherosclerosis, endothelial dysfunction, allergic rhinitis, dermatitis, psoriasis, cystic fibrosis, inflammatory bowel diseases, interstitial cystitis, migraines, angina, chronic prostatitis, sun burn, periodontal disease, multiple sclerosis, uveitis, post-angioplasty restenosis, glomerulonephritis, gastrointestinal allergies, nephritis, conjunctivitis, chronic obstructive pulmonary disease, occupational asthma, eczema, bronchitis, hay fever, hives, allergic disorders and for conditions like wheezing, dyspnea, non-productive cough, chest tightness, neck muscle tightness, rapid heart rate, chest pain, joint pain, joint disorders, collagen degradation by UV irradiation, skin-wrinkling and skin-aging and several other conditions associated thereof in mammals.

Non-limiting examples of arthritis include rheumatoid (such as soft-tissue rheumatism and non-articular rheumatism, fibromyalgia, fibrositis, muscular rheumatism, myofascial pain, humeral epicondylitis, frozen shoulder, Tietze's syndrome, fascitis, tendinitis, tenosynovitis, bursitis), juvenile chronic, joint disorders, spondyloarthropathies (ankylosing spondylitis), osteoarthritis, hyperuricemia and arthritis associated with acute gout, chronic gout and systemic lupus erythematosus and degenerative arthritis.

In a further embodiment, the present invention provides the process for producing extracts or fractions and their compositions from *Terminalia chebula*, *Curcuma longa* and *Boswellia serrata* non-acidic resin extract (BNRE) plant parts including but not limited to bark, root, stem, leaves, fruit, gum resin, rhizome and mixtures thereof.

In another embodiment, the solvents that can be used for preparing the extracts or fractions of the herbs can be selected from chlorinated solvents, such as, dichloromethane and dichloroethane, C1-C5 alcohols such as ethanol, methanol; water and mixtures thereof; esters such as ethyl acetate; C1 to C7 hydrocarbons; hydroalchohol and mixtures thereof.

In yet another embodiment of the present invention, the synergistic compositions containing extracts or fractions derived from *Terminalia chebula* and *Curcuma longa* and *Boswellia serrata* non-acidic resin extract (BNRE) contain optionally one or more of pharmaceutically or nutraceutically or dietetically acceptable excipient(s) or diluents or salt(s) or additive(s).

In yet another embodiment of the present invention, the synergistic compositions derived from *Terminalia chebula* and *Curcuma longa* and *Boswellia serrata* non-acidic resin extract (BNRE) are produced from aqueous, alcoholic or hydro alcoholic extracts.

In yet another embodiment of the present invention, the synergistic compositions derived from *Terminalia chebula* and *Curcuma longa* and *Boswellia serrata* non-acidic resin extract (BNRE) and *Boswellia serrata* extract standardized to 75%-85% total acids by volumetric assay which contain at least 5% 3-O-acetyl-11-keto-β-boswellic acid (AKBA).

In yet another embodiment of the present invention, the synergistic compositions comprises 25-45% of *Terminalia chebula,* 15-25% of *Curcuma longa* and 15-25% of *Boswellia serrata* non-acidic resin extract (BNRE) and 15-25% of *Boswellia serrata* extract standardized to 75%-85% total acids by volumetric assay which contain at least 5% 3-O-acetyl-11-keto-β-boswellic acid (AKBA) and 5-15% of excipients In yet another embodiment of the present invention, the synergistic compositions composition comprises 36% of *Terminalia chebula* extract, 18% of *Curcuma longa* extract, 18% *Boswellia serrata* non-acidic resin extract (BNRE) and 18% of *Boswellia serrata* extract standardized to 75%-85% total acids by volumetric assay which contain at least 5% 3-O-acetyl-11-keto-β-boswellic acid (AKBA) and 10% of excipients.

The other embodiments of the present invention further provides the usage of the said synergistic compositions as it is or in comminuted form and/or in unmodified form as granules or powder or paste or the active ingredients are formulated into a solid, semi-solid or liquid dosage form by adding a conventional biologically or pharmaceutically acceptable salt(s) or additive(s) or excipient(s).

In a further embodiment, the invention provides therapeutically effective amount of the novel compositions of the present invention which can be administered in a specific dosage form such as orally, topically, transdermally, parenterally or in the form of a kit to a subject or patient in need thereof. Specific dosage form for formulation of the compositions of the present invention includes but not limited to oral agents such as tablets, soft capsules, hard capsules, pills, granules, powders, infusion solution, injection solution, cream, gel, emulsions, ointment, enema, medicinal pack, food supplement, emulsions, suspensions, syrups, pellets, inhalers, mouth sprays and the like; and parenteral agents such as injections, drops, suppositories and the like.

In other preferred embodiment, the present invention provides a method for the prevention, control and treatment of one or more disease conditions related to or associated with inflammation which include but not limited to asthma, arthritis inflammatory bowel disease, rheumatoid arthritis, juvenile rheumatoid arthritis, psoriatic arthritis, osteoarthritis, refractory rheumatoid arthritis, chronic non-rheumatoid arthritis, atherosclerosis, endothelial dysfunction, allergic rhinitis, dermatitis, psoriasis, cystic fibrosis, inflammatory bowel diseases, interstitial cystitis, migraines, angina, chronic prostatitis, sun burn, periodontal disease, multiple sclerosis, uveitis, post-angioplasty restenosis, glomerulonephritis, gastrointestinal allergies, nephritis, conjunctivitis, chronic obstructive pulmonary disease, occupational asthma, eczema, bronchitis, hay fever, hives, allergic disorders and for conditions like wheezing, dyspnea, non-productive cough, chest tightness, neck muscle tightness, rapid heart rate, chest pain, joint pain, collagen degradation by UV irradiation, skin-wrinkling and skin-aging and several other conditions associated thereof in mammals, wherein the method comprises supplementing said mammal with an effective amount of synergistic composition containing extracts or fractions derived from *Terminalia chebula* fruit and *Curcuma longa* root and non-acidic resin extract derived *Boswellia serrata.*

In a further embodiment of the present invention, the compositions may further comprises an effective amount(s) of one or more pharmaceutical or nutraceutical or dietetically acceptable agents including but not limited to antioxidant(s), adaptogen(s), anti-inflammatory agent(s), anti-diabetic agent(s), antiobese agent(s), anti-atherosclerotic agent(s), bio-protectants and/or bio-availability enhancer(s) and trace metals or an excipient(s) or pharmaceutically acceptable salt(s) or additive(s) and the compositions or mixtures thereof to form a formulation(s) that can be administered using any of the methods described above.

The examples of pharmaceutically acceptable anti-inflammatory agents employed in the present invention include, but are not limited to prednisolone, hydrocortisone, methotrexate, sulfasalazine, naproxen, diclofenac and ibuprofen.

The examples of the biologically or pharmaceutically acceptable carriers employed in the present invention include, but are not limited to, surfactants, excipients, binders, diluents, disintegrants, lubricants, preservatives, stabilizers, buffers, suspensions and drug delivery systems.

Preferred examples of solid carriers or diluents or excipients include but not limited to glucose, fructose, sucrose, maltose, yellow dextrin, white dextrin, aerosol, microcrystalline cellulose, syloid, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives.

Preferred examples of liquid carriers (diluents) include, distilled water, saline, aqueous glucose solution, alcohol (e.g. ethanol), propylene glycol and polyethylene glycol; and oily carriers such as various animal and vegetable oils, white soft paraffin, paraffin and wax.

In alternative aspect of the invention, the inventive compositions of the present invention are delivered in the form of controlled release tablets, using controlled release polymer-based coatings by the techniques including nanotechnology, microencapsulation, colloidal carrier systems and other drug delivery systems known in the art. The said compositions can be designed for once a daily administration or multiple administrations per day.

In accordance to the present invention, the compositions of the present invention can also be formulated into or added to existing or new food and beverage form(s) such as solid foods like cereals, baby food(s), chocolate or nutritional bars, semisolid food like cream or jam, or gel, refreshing beverage, coffee, tea, milk-contained beverage, dairy products, lactic acid bacteria beverage, soup, drop, candy, chewing gum, chocolate, gummy candy, yoghurt, ice cream, pudding, soft adzuki-bean jelly, jelly, cookie, bakery products and the like. These various compositions or preparations or foods and drinks are useful as a healthy food for the treatment and/or prevention of inflammation and/or one or more of disease conditions associated with or related to inflammation including but not limited to asthma, arthritis inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, atherosclerosis, vasculitis, ulcerative colitis, psoriasis, adult respiratory distress syndrome, diabetes, metabolic disorders, delayed-type hypersensitivity in skin disorders and Alzheimer's disease.

Various exemplary embodiments of the invention provides that the amount of present synergistic compositions to be administered or supplemented to humans or mammals may not be uniform and varies depending on the nature of the formulation and suggested human or animal dosage of the extract or the fractions, but preferably, within a range from 0.1 to 750 mg/kg body weight per day, more preferably about 0.5 to 500 mg/kg body weight.

Another embodiment of the invention provides that the quantity of the present inventive compositions in the above-mentioned various formulations, food and beverage compositions may also not be uniform and varies depending on the nature of the formulation and suggested human or animal dosage of the compositions, for example, about 0.001% to 99%, more preferably about 0.1 to 90 wt %.

In one of the preferred embodiments, the concentration of *Terminalia chebula* extract varies in the range of 20% to 75% by weight.

In another preferred embodiment, the concentration of *Curcuma longa* extract varies in the range of 10% to 40% by weight. In another preferred embodiment, the concentration of *Curcuma longa* extract varies in the range of 15% to 40% by weight.

In yet another preferred embodiment, the concentration of *Boswellia serrata* non-acidic resin extract (BNRE) varies in the range of 10% to 40% by weight.

In still another embodiment, the synergistic composition comprises *Terminalia chebula* by weight ranging from 20% to 75%, *Curcuma longa* by weight ranging from 10% to 40% and *Boswellia serrata* non-acidic resin extracts (BNRE) by weight ranging from 10% to 40%.

In some embodiments, the synergistic composition comprises *Terminalia chebula* by weight ranging from 20% to 75%, *Curcuma longa* by weight ranging from 15% to 40% and *Boswellia serrata* non-acidic resin extracts (BNRE) by weight ranging from 10% to 40%.

In yet another embodiment, the synergistic composition comprises *Terminalia chebula* by weight ranging from 25% to 65%, *Curcuma longa* by weight ranging from 12% to 30% and *Boswellia serrata* non-acidic resin extracts (BNRE) by weight ranging from 12% to 30%.

Further embodiment of the invention provides that the amount of the present synergistic composition(s) varies in the range of 1% to 100% by weight based on the total weight of the composition.

In another embodiment, the invention further comprises; mixing the compositions of the present invention with various components used in the animal feed for the purpose of curing, preventing or treating inflammation and several inflammation associated or related diseases including asthma, atherosclerosis and arthritis and the like.

The form of the composition or formulation to be added to animal feed is not specifically limited and may be added it is, or as a composition(s), to various cooked and processed food products. The quantity may be the same as that used in case of food products. Similarly, the ingredients may also be added during or after preparation of the animal feeds.

In accordance to the present invention, the compositions of the present invention can also be formulated into any dietary supplement, food and beverage forms for human and animal applications.

In another preferred embodiment, the invention provides a method for treating an inflammation, arthritis and joint disease in a patient in need thereof comprising administering to the patient an effective amount of novel synergistic composition(s) comprising a combinations of *Terminalia chebula* extract, *Curcuma longa* extract and *Boswellia serrata* non-acidic resin extract (BNRE) optionally comprises at least one ingredient selected from plant derived anti-inflammatory agents, pharmaceutically or nutraceutical or dietetically acceptable carriers/excipients.

The method for treating an inflammation, arthritis and joint disease are selected from rheumatoid arthritis, psoriatic arthritis, osteoarthritis, refractory rheumatoid arthritis, chronic non-rheumatoid arthritis, osteoporosis/bone resorption, collagen degradation, gouty arthritis, lupus or juvenile arthritis and Joint pain.

The method of treating an inflammatory condition which include but not limited to rheumatoid arthritis, psoriatic arthritis, osteoarthritis, refractory rheumatoid arthritis, chronic non-rheumatoid arthritis, osteoporosis/bone resorption, collagen degradation, gouty arthritis, lupus or juvenile arthritis and Joint pain in a mammal, where in the method comprises, supplementing the mammal in need there off a synergistic compositions comprising 25-45% of *Terminalia chebula*, 15-25% of *Curcuma longa* and 15-25% of *Boswellia serrata* non-acidic resin extract (BNRE) and 15-25% of *Boswellia serrata* extract standardized to 75%-85% total acids by volumetric assay which contain at least 5% 3-O-acetyl-11-keto-β-boswellic acid (AKBA) and 5-15% of excipients.

In another preferred embodiment, the invention provides use of novel synergistic composition(s) comprising a combinations of *Terminalia chebula* extract, *Curcuma longa* extract and *Boswellia serrata* non-acidic resin extract (BNRE) optionally comprises at least one ingredient selected from plant derived anti-inflammatory agents, pharmaceutically or nutraceutical or dietetically acceptable carriers/excipients, for treating an inflammation, arthritis and joint disease.

The following examples, which include preferred embodiments, will serve to illustrate the practice of this invention, and it being understood that the particulars shown are by way of example and for purpose of illustrative discussion of preferred embodiments of the invention and they are not to limit the scope of the invention.

Example 1: Preparation of *Terminalia chebula* Water Extract

Dried fruits of plant *Terminalia chebula* (1 Kg) were pulverized to coarse powder, extracted with water (5 L) at 80° C. for 1.5 hour. The extraction process was repeated thrice using water (5, 3.5, and 3.5 L) in 1:3-1:5 ratio w/v with respect to plant material. All the extracts were combined, the combined aqueous extracts were fine filtered, and the clear extract was evaporated to dryness on a climbing film evaporator at 50-60° C. to obtain 300 g of *Terminalia chebula* extract.

Example 2: Preparation of *Terminalia chebula* Alcohol Extract

Dried fruits of plant *Terminalia chebula* (0.1 Kg) were pulverized to coarse powder, extracted with alcohol for 1 hrs at Rt/at reflux temp. Extraction process repeated thrice using with Alcohol are in the ratio 1:12-1:17 W/V with respect to the plant material. All the extracts were combined, the combined alcohol extracts were fine filtered, and the clear extract was evaporated under at 40° C. under vacuum to give dry powder (290 gm).

Example 3: Preparation of *Curcuma longa* Alcohol Extract

Dried rhizomes of plant *Curcuma longa* (1 Kg) was pulverized to coarse powder, extracted with 5 L of alcohol such as ethanol, methanol or mixtures thereof at temperature range 60-65° C. for 2-3 hrs. Extraction process repeated thrice using alcohol in the ratio 1:4-1:5 w/v with respect to the plant material. All the three extractions were combined and fine filtered. The filtrate was evaporated to dryness under reduced pressure at 40-50° C. to obtain 70 g of *Curcuma longa* extract when methanol is the extraction medium.

Example 4: Preparation of *Boswellia serrata* Non-Acidic Resin Extract (BNRE)

The *Boswellia serrata* gum resin (100 g) was dispersed in 600 mL of methyl isobutyl ketone (MIBK) solvent and stirred at room temperature for 6.0 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are removed from the oily residue under vacuum at 120-150° C. to obtain *Boswellia serrata* non-acidic resin extract or BNRE as a viscous oil (12 g).

The aqueous alkali solution containing the acidic compounds was acidified using concentrated HCl solution. The precipitate obtained was filtered and solid dried under vacuum to obtain *Boswellia serrata* acidic extract, which showed 75%-85% total acids by volumetric assay.

The above procedure can also be performed using ethyl acetate in place of MIBK to obtain non-acidic resin extract and acidic resin extracts.

Alternatively, the gum resin (250 g) collected from *Boswellia serrata* was extracted with methanol (300 mL×3) and the combined methanol extract was concentrated. The residue (50 g) was dissolved in ethyl acetate (400 mL) and extracted thrice with 2N KOH (3×100 mL). The organic layer was washed with water (2×200 mL) and brine (200 mL) and evaporated to obtain *Boswellia* oil. The volatile compounds were evaporated from the oil under vacuum at 120-150° C. to obtain 22 g of *Boswellia serrata* non-acidic resin extract (BNRE).

Example 5: Preparation of *Boswellia serrata* Acidic Extract

Raw material 0.1 kg was extracted with 800 mL of Ethyl Acetate (EtOAc) under reflux for 3 hrs. Extraction process repeated with two times using EtOAc in the 1:6 w/v ratios with respect to plant material. EtOAc soluble extractives were treated with 2.8% Aq. KOH (3×1:1 v/v with respect with EtOAc extract). The mixture was stirred for 30 min and settled for 2 hrs. Separate the top EtOAc layer and washed successively with water and brine 1:4 v/v and 1:2 v/v with respect to EtOAc extract respectively. Top layer (Ethyl acetate) was concentrated at 70-75° C. for 3-4 hrs and further concentrated at 140° C. under high vacuum for 2 hrs (HPR5:1).

Bottom layer (base layer) was concentrated at 70-75° C. under vacuum for 3 hrs. and diluted with water. Adjusted pH to 1.45 with 10% HCl and the precipitate filtered and washed with water till neutral pH. Wet cake dried under vacuum for 20 hrs to obtain acidic gum resin extract (130 gm).

Example 6: Composition-1

The composition-1 was prepared by combining the water extract of *Terminalia chebula*, methanol extract of *Curcuma longa* and *Boswellia serrata* non-acidic resin extract (BNRE) in the ratio of 2:1:1 (50%:25%:25%).

Example 7: Composition-2

The composition-2 was prepared by combining the water extract of *Terminalia chebula*, methanol extract of *Curcuma longa* and *Boswellia serrata* non-acidic resin extract (BNRE) in the ratio of 7.5:1.5:1.0 (75%:15%:10%).

Example 8: Composition-3

The composition-3 was prepared by combining the water extract of *Terminalia chebula*, methanol extract of *Curcuma longa* and *Boswellia serrata* non-acidic resin extract (BNRE) in the ratio of 7.5:1.0:1.5 (75%:10%:15%).

Example 9: Composition-4

The composition-4 was prepared by combining the water extract of *Terminalia chebula*, methanol extract of *Curcuma longa* and *Boswellia serrata* non-acidic resin extract (BNRE) in the ratio of 1:2:2 (20%:40%:40%).

Example 10: Composition-5

The composition-5 was prepared by combining the water extract of *Terminalia chebula*, methanol extract of *Curcuma longa*, *Boswellia serrata* non-acidic resin extract (BNRE) and *Boswellia serrata* extract standardized to 75%-85% total acids by volumetric assay which contain 5% 3-O-acetyl-11-keto-β-boswellic acid (AKBA) in the ratio of 2:1:1:1 (40%:20%:20%:20%).

Example 11: Composition-6

The composition-6 was prepared by combining the water extract of *Terminalia chebula*, methanol extract of *Curcuma longa*, *Boswellia serrata* non-acidic resin extract (BNRE), and excipients [Microcrystalline cellulose (MCC) and Syloid] in the ratio of 2:1:1:2 (34%:17%:17%:32%).

Example 12: Composition-7

The composition-7 was prepared by combining the water extract of 36 g of *Terminalia chebula*, 18 g of methanol extract of *Curcuma longa*, 18 g of *Boswellia serrata* non-acidic resin extract (BNRE), 18 g of *Boswellia serrata* extract standardized to 75%-85% total acids by volumetric assay which contain 5% 3-O-acetyl-11-keto-β-boswellic acid (AKBA) and 10 g of excipients[Microcrystalline cellulose (MCC) and Syloid], so that their percentages in the composition are 36%, 18%, 18%, 18% and 10% respectively.

Example 13: 5-Lipoxygenase Enzyme (5-LOX) Inhibitory Activity

5-Lipoxygenase enzyme (5-LOX) inhibitory activity was measured using the method of Lip Yong Chung et al., (Pharmaceutical Biology, Vol. 47 (12), 1142-1148, 2009). The assay mixture contained 80 μM linoleic acid and sufficient amount of potato 5-lipoxygenase in 50 mM TrisHCl buffer (pH 7.4). 5 μL of 5-LOX enzyme was added to 175 μL of 50 mM TrisHCl buffer. The reaction was initiated by the addition of 5 μL linoleic acid (final conc. 140 μM) in 50 mM TrisHCl buffer followed by incubation at 250

C in dark 20 min. The total volume of the reaction mixture is 185 μL. The assay was terminated by the addition of 65 μL freshly prepared fox reagent. After incubation for 20 min the absorbance was read using Xmark Micro plate spectrophotometer (BIO-RAD) at 595 nm. The reaction was monitored for 120 sec and the inhibitory potential of the test substances i.e., extracts and compositions was measured by incubating various concentrations of test substances two minutes before the addition of linoleic acid. All assays were performed three times. Percentage inhibition of 5-Lipoxygenase activity was calculated by comparing slope of the curve obtained for test substances with that of the control. The half maximal inhibitory concentrations (IC50s) of *Terminalia chebula* extract, *Curcuma longa* extract, *Boswellia serrata* non-acidic resin extract (BNRE), *Boswellia serrata* acidic extracts standardized to 75-85% total acids and around 5% 3-O-acetyl-11-keto-β-boswellic acid (AKBA) and compositions are summarized in Table 1.

TABLE 1

5-Lipoxygenase enzyme (5-LOX) inhibitory activity

| S. No. | Tested substance | IC$_{50}$ (μg/ml) |
|---|---|---|
| 1 | *Terminalia chebula* extract | 26.41 |
| 2 | *Curcuma longa* extract | 19.53 |
| 3 | *Boswellia serrata* non acidic resin extract (BNRE) | 16.40 |
| 4 | *Boswellia serrata* extract 5% AKBA | >100 |
| 5 | Composition-1 | 14.84 |
| 6 | Composition-2 | 12.89 |
| 7 | Composition-3 | 23.43 |
| 8 | Composition-4 | 14.45 |
| 9 | Composition-7 | 12.35 |

The above 5-lipoxygenase inhibitory activities in the Table 1, clearly show the synergistic efficacy of the compositions comprising *Terminalia chebula* extract, *Curcuma longa* extract and *Boswellia serrata* non-acidic resin extract (BNRE), and those optionally *Boswellia serrata* acidic extract standardized to 75-85% total acids and/or 5% 3-O-acetyl-11-keto-β-boswellic acid (AKBA) in inhibiting the 5-lipoxygenase enzyme activity. This observation suggests that composition of the extracts showed greater 5-lipoxygenase inhibitory activity than the individual extracts. For example, the IC50 values of *T. chebula* extract, *C. longa* extract, BNRE and *Boswellia serrata* acidic extract are 25.41 μg/ml, 19.53 μg/ml, 16.40 μg/ml and >100 μg/ml respectively, whereas, the composition-1, composition-2, composition-3, composition-4 and composition-7 exhibited 5-lipoxygenase inhibitory activity with an IC50 value of 14.84 μg/ml, 12.89 μg/ml, 23.43 μg/ml, 14.45 μg/ml and 12.35 μg/ml respectively. The 5-lipoxygenase inhibitory activity with the compositions is higher than that of the individual extracts.

Example 14: Interleukin 1 (IL-1β) Inhibitory Activity

Inhibition of lipopolysaccharide (LPS)-induced IL-1β production by extracts and compositions was evaluated in Phorbol 12-myristate 13-acetate (PMA) differentiated THP-1 human monocytes. Briefly, the THP-1 cells were differentiated with 20 nM of PMA and incubated further for 48 hrs at 37° C. in a 5% CO2 incubator. Cells were washed with fresh DMEM containing 10% fetal calf serum (FCS) and pretreated with different concentrations of extracts or compositions. Thereafter, the cells were treated with Lipo polysaccharides (LPS) (10 ng/ml) and incubated further for 4 hrs. at 37° C. in a 5% CO2 incubator. The supernatant was harvested and the IL-1β concentration secreted into the cell free culture supernatants was measured using human IL-1β ELISA Kit (R&D System, Minneapolis, Minn., USA). Percentage of IL-1β inhibition of extracts or compositions was calculated from the formula: {(Conc. of IL-1β in induced−Conc. of IL-1β in the tested extracts or compositions)×100}÷Conc. of IL-1β in LPS-induced THP-1 human monocytes. The data for inhibition of IL-1β production by extracts or compositions is depicted in Table 2.

The synergistic efficacy was substantiated by the evaluation of the biomarker Interleukin-1beta, (IL-1β). The treatment groups supplemented with composition-1, composition-2, composition-4 and composition-7 showed significantly better activity in reducing the serum biomarker, IL-1β, compared to the additive effect contributed by the individual ingredients *T. chebula* extract, *C. longa* extract, BNRE and *Boswellia serrata* acidic extract as shown in Table 2.

TABLE 2

Interleukin 1 (IL-1β) inhibitory activity

| S. No. | Tested substance (50 μg/ml) | Inhibition of IL-1βProduction (%) |
|---|---|---|
| 1 | *Terminalia chebula* extract | 3.36 |
| 2 | *Curcuma longa* extract | 23.65 |
| 3 | *Boswellia serrata* non acidic resin extract (BNRE) | 5.16 |
| 4 | *Boswellia serrata* extract 5% AKBA | 4.45 |
| 5 | Composition-1 | 22.88 |
| 6 | Composition-2 | 19.54 |
| 7 | Composition-4 | 20.23 |
| 8 | Composition-7 | 30.20 |

Referring to Table 2, Composition-1 is administered in a total amount of 50 μg/ml, and comprises 50% of the extract of *Terminalia chebula* (25 μg/ml), 25% of the methanol extract of *Curcuma longa* (12.5 μg/ml), and 25% of the *Boswellia serrata* non-acidic resin extract (BNRE; 12.5 μg/ml). If the individual components of Composition-1 had an additive effect, 25 μg/ml of *Terminalia chebula* extract would be expected to be 50% as active as 50 μg/ml of pure *Terminalia chebula* extract. Similarly, 12.5 μg/ml of *Curcuma longa* extract and 12.5 μg/ml of *Boswellia serrata* non-acidic resin extract would be expected to be 25% as active as 50 μg/ml of the pure extracts. Based on this, Composition-1 would be expected to have a total inhibition of IL-1β production of 8.88%, calculated as follows:

(0.5×3.36% IL-1β inhibition)+(0.25×23.65% IL-1β inhibition)+(02.5×5.16% IL-1β inhibition)=expected IL-1β inhibition However, Composition-1 has a total inhibition of IL-1β production of 22.88%, which is significantly greater than would be expected from an additive effect. Thus, Composition-1 shows synergism with regard to inhibition of IL-1β production. Similar calculations demonstrate that Composition-2, Composition-4, and Composition-7 also show synergism.

This unexpected result clearly indicate that, the synergistic activity of the compositions comprising *Terminalia chebula* extract, *Curcuma longa* extract and *Boswellia serrata* non-acidic resin extract (BNRE) and 3-O-acetyl-11-keto-β-boswellic acid (AKBA) in inhibiting the biomarker Interleukin-1beta (IL-1β) and suggest that compositions are useful for prevention, treatment, inhibition or controlling inflammation and/or immune related diseases mediated through pro-inflammatory cytokines/chemokines when compare with the individual extracts.

Example 15: Inhibition of Tumor Necrosis Factor-α (TNF-α) In Vitro

The anti-inflammatory activities of extracts and compositions were assessed in a cell based in vitro assay. Briefly, THP-1 human monocytes cells were washed and re-suspended in phenol red free Dulbecco's Modified Eagle's Medium (DMEM) supplemented with 1% fetal Bovine serum (FBS). Equal number of cells was added to each well of a 96-well cell culture plate and the cells were pretreated for 2 h with various concentrations of test substances (ranging from 0.5 to 50 µg/ml; solutions prepared in culture medium from a stock solution containing 50 mg/1 mL DMSO of each test sample) of extracts or compositions. The inflammatory response was induced by treatment with 100 ng/ml of LPS for 4 h at 37° C. in presence of 5% CO2. The vehicle control culture wells received 0.1% DMSO in culture medium. The cell free culture supernatants were collected and assessed for secretary pro-inflammatory cytokine, TNFα. The TNF-α concentration was quantitatively measured by highly specific and sensitive Enzyme Immuno Assay (EIA) kit supplied by R&D Systems, USA. The enzyme immuno assay was performed based on the protocol provided by the vendor. The inhibitory concentration for 50% inhibition (IC50) of TNF-α was determined from a plot drawn for ingredient concentration against TNF-α level. Table 3 shows concentrations of compositions for 50% inhibition of TNF-α ($IC_{50}$) in cell based in vitro model.

TABLE 3

| | TNFα activity | |
|---|---|---|
| S. No. | Tested substance (20 µg/ml) | TNFα activity (% of inhibition) |
| 1 | Composition-1 | 51.16 |
| 2 | Composition-2 | 72.78 |
| 3 | Composition-3 | 28.7 |
| 4 | Composition-4 | 91.3 |
| 5 | Composition-5 | 84.87 |
| 6 | Composition-6 | 56.01 |
| 7 | Composition-7 | 79.55 |

Example 16: Inhibition of Matrix Metalloproteinase-3 (MMP-3) Activity

Inhibition of MMP-3 production by extracts and compositions was evaluated in TNFα induced SW982 human synovial cells. Briefly, the SW982 cells were cultured in DMEM with 2 mM Glutamine, 100 U/mL penicillin, 100 mg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 1% fetal bovine serum. Extracts or Compositions were serially diluted in medium, ranging from 5 to 100 ng/ml and were pre-incubated with cells for 2 hour at 5% CO2 at 37° C., and then stimulated with 10 ng/ml human recombinant TNFα (R&D System, Minneapolis, Minn.) for 24 hours. The cell free culture supernatants were harvested and used to measure MMP-3 production by ELISA development kit (R&D System, Minneapolis, Minn., USA). The MMP-3 concentration in cell free culture supernatant was estimated quantitatively by interpolating the optical densities into the standard curve generated from known concentrations of MMP-3. The inhibitory concentration for 50% inhibition (IC50) of MMP-3 was calculated from the plot constructed by plotting percentage inhibition against concentration (Table 4).

TABLE 4

| | MMP-3activity | |
|---|---|---|
| S. No. | Tested substance (20 µg/ml) | MMP-3activity (% of inhibition) |
| 1 | *Terminalia chebula* extract | 35.53 |
| 2 | *Curcuma longa* extract | 44.4 |
| 3 | *Boswellia serrata* non acidic resin extract (BNRE) | 45.22 |
| 4 | *Boswellia serrata* extract 5% AKBA | 12.98 |
| 5 | Composition-7 | 66.92 |

Example 17: The In-Vivo Anti-Inflammatory Activity of Composition-1

The in-vivo anti-inflammatory activity of composition-1, comprising the water extract of 50 g of *Terminalia chebula*, 25 g of methanol extract of *Curcuma longa*, 25 g of *Boswellia serrata* non-acidic resin extract (BNRE), so that their percentages in the composition are 50%, 25% and 25% respectively was evaluated by an in-vivo study in Freund's Complete Adjuvant induced arthritis model of Sprague Dawley (SD) rats.

Prednisolone was used as a positive control. The healthy male SD rats were selected and randomly divided into four groups containing six animals per group. The treatment group rats were supplemented daily with 200 mg/kg body weight of Composition-1 for 35 days. The positive control group was supplemented daily with Prednisolone at 10 mg/kg body weight. All supplements were diluted in 10 mL of 1% CMC for administration. The animals of control group received same volume of 1% CMC. At the 7th day, Freund's Complete Adjuvant (FCA) was injected subcutaneously in the sub-plantar region of the left hind paw of each animal. Paw volumes and weight bearing capacities were respectively measured using Plethysmography equipment and Incapacitance Meter on the day of FCA injection and on 35th day of treatment. The difference in volume of paw edema is considered as the inflammatory response. The in-vivo anti-inflammatory response of Composition-1 was estimated by calculating the percentage inhibition of paw edema when compared to the CMC supplemented control The treatment groups supplemented with 200 mg/kg body weight of Composition-1 showed 40.35% reduction in paw edema in Table 5.

TABLE 5

| S. No | Test compound | % inhibition of Paw edema |
|---|---|---|
| 1 | Composiition-1 | 40.35% |
| 2 | Prednisolone | 72.73% |

The improvement in percent weight bearing is considered as improvement in efficacy and the results were presented in Table 6.

TABLE 6

| S. No | Test compound | Percent Weight Bearing on Left Hind Limb |
|---|---|---|
| 1 | Normal Animals | 49.30% |
| 2 | Disease control | 22.47% |
| 3 | Compoisition-1 | 30.35% |

The above in-vivo anti-inflammatory activity values in the Table 5 and Table 6, Supplementation of composition-1 (300 mpk) for 35 days, showed a statistically significant (p<0.05) inhibition of paw edema with 40.35% by the end of day 35 as compared to AIA control.

Supplementation of composition-1 (300 mpk) showed moderate improvement in percentage weight bearing capacity in adjuvant induced arthritis rats.

These results together suggests that oral administration of composition-1 reduces paw edema and improves weight bearing capacity in adjuvant induced arthritis in Sprague Dawley rats.

Example 18: The In-Vivo Anti-Inflammatory Activity of Composition-7

The in-vivo anti-inflammatory activity of composition-7, comprising the water extract of 36 g of *Terminalia chebula*, 18 g of methanol extract of *Curcuma longa*, 18 g of *Boswellia serrata* non-acidic resin extract (BNRE), 18 g of *Boswellia serrata* extract standardized to 75%-85% total acids by volumetric assay which contain 5% 3-O-acetyl-11-keto-β-boswellic acid (AKBA) and 10 g of excipients [Microcrystalline cellulose (MCC) and Syloid], so that their percentages in the composition are 36%, 18%, 18%, 18% and 10% respectively was evaluated by an in-vivo study in Freund's Complete Adjuvant induced arthritis model of Sprague Dawley rats.

Prednisolone was used as a positive control. The healthy male SD rats were selected and randomly divided into four groups containing six animals per group. The treatment group rats were supplemented daily with 200 mg/kg body weight of Composition-7 for 35 days. The positive control group was supplemented daily with Prednisolone at 10 mg/kg body weight. All supplements were diluted in 10 mL of 1% CMC for administration. The animals of control group received same volume of 1% CMC. At the 7th day, Freund's Complete Adjuvant (FCA) was injected subcutaneously in the sub-plantar region of the left hind paw of each animal. Paw volumes and weight bearing capacities were respectively measured using Plethysmography equipment and Incapacitance Meter on the day of FCA injection and on 35th day of treatment. The difference in volume of paw edema is considered as the inflammatory response. The in-vivo anti-inflammatory response of Composition-7 was estimated by calculating the percentage inhibition of paw edema when compared to the CMC supplemented control.

The treatment groups supplemented with 200 mg/kg body weight of Composition-7 showed 44.34% reduction in paw edema (Table 7).

TABLE 7

| S. No | Test compound | % inhibition of Paw edema |
|---|---|---|
| 1 | Compoisition-7 | 44.34% |
| 2 | Prednisolone | 68.67% |

The improvement in percent weight bearing is considered as improvement in efficacy and the results were presented in Table 8.

TABLE 8

| S. No | Test compound | Percent Weight Bearing on Left Hind Limb |
|---|---|---|
| 1 | Normal Animals | 50.85% |
| 2 | Disease control | 25.73% |
| 3 | Composition-7 | 45.33% |

The above in-vivo anti-inflammatory activity values in the Table 7 and Table 8 indicates, animals administered with composition-7 (200 mpk p.o.) showed 44.34% reduction in paw edema, this reduction in paw edema is statistically significant (p<0.05) as compared to AIA control. Administration of composition-7 (200 mpk p.o.) also resulted 45.33% improvement in weight bearing capacity and this improvement in weight bearing capacity is statistically significant (p<0.05) as compared to AIA control. These results together suggests that oral administration of composition-7 reduces paw edema and improves weight bearing capacity in adjuvant induced arthritis in Sprague Dawley rats.

It will be appreciated to those of ordinary skill in the art that changes could be made to the embodiments described above without departing from the broad inventive concept thereof. It is understood, therefore, that this invention is not limited to the particular embodiments or examples disclosed, but is intended to cover modifications within the objectives and scope of the present invention.

What is claimed is:

1. A method for treating an inflammation, arthritis, or a joint disease in a patient in need thereof, comprising administering to the patient an effective amount of an herbal composition, wherein the herbal composition comprises:
   from 20% by weight to 75% by weight of an extract of *Terminalia chebula*;
   from 10% by weight to 40% by weight of an extract of *Curcuma longa*; and
   from 10% by weight to 40% by weight of a non-acidic, water-immiscible organic solvent extract of a *Boswellia serrata* resin,
   based on the total weight of the *Terminalia chebula*, *Curcuma longa*, and *Boswellia serrata* extracts.

2. The method according to claim 1, wherein the non-acidic, water-immiscible organic solvent extract of the *Boswellia serrata* resin is a product obtained by a process comprising:
   extracting *Boswellia serrata* gum resin with a water-immiscible organic solvent to obtain an organic solution;
   extracting the organic solution with aqueous alkali to remove boswellic acids from the organic solution; and
   removing the water-immiscible organic solvent from the organic solution to obtain an organic solvent extract.

3. The method according to claim 1, wherein the non-acidic, water-immiscible organic solvent extract of the *Boswellia serrata* resin is a product obtained by a process comprising:
   extracting *Boswellia serrata* gum resin with a water-immiscible organic solvent to obtain an organic solution;
   extracting the organic solution with aqueous alkali to remove boswellic acids from the organic solution;

removing the water-immiscible organic solvent from the organic solution to obtain an organic solvent extract; and removing volatile components from the organic solvent extract under vacuum to obtain said non-acidic, water-immiscible organic solvent extract.

4. The method according to claim 1, wherein the herbal composition further comprises at least one ingredient selected from the group consisting of:
plant derived anti-inflammatory agents,
pharmaceutically, nutraceutically, or dietetically acceptable carriers, and
pharmaceutically, nutraceutically, or dietetically acceptable excipients.

5. The method according to claim 4, wherein the carriers and excipients are selected from the group consisting of surfactants, binders, diluents, disintegrants, lubricants, preservatives, stabilizers, buffers, suspensions, and drug delivery systems.

6. The method according to claim 1, wherein:
the extract of *Terminalia chebula* is prepared from dried fruits of *Terminalia chebula*;
the extract of *Curcuma longa* is prepared from dried rhizomes of *Curcuma longa*; and
the non-acidic, water-immiscible organic solvent extract of the *Boswellia serrata* resin is prepared from a gum resin of *Boswellia serrata*.

7. The method according to claim 1, wherein the herbal composition further comprises:
from 0% by weight to 20% by weight of a *Boswellia serrata* extract which contains at least 5% 3-O-acetyl-11-keto-β-boswellic acid (AKBA),
based on the total weight of the *Terminalia chebula, Curcuma longa*, and *Boswellia serrata* extracts.

8. The method according to claim 1, wherein the herbal composition comprises:
from 25% by weight to 65% by weight of the extract of *Terminalia chebula*;
from 12% by weight to 30% by weight of the extract of *Curcuma longa*; and
from 12% by weight to 30% by weight of the non-acidic, water-immiscible organic solvent extract of the *Boswellia serrata* resin,
based on the weight of the composition.

9. The method according to claim 1, wherein the herbal composition comprises:
from 25% by weight to 45% by weight of the extract of *Terminalia chebula*;
from 15% by weight to 25% by weight of the extract of *Curcuma longa*;
from 15% by weight to 25% by weight of the non-acidic, water-immiscible organic solvent extract of the *Boswellia serrata* resin, and
from 15% by weight to 25% by weight of a *Boswellia serrata* extract which contains at least 5% 3-O-acetyl-11-keto-β-boswellic acid (AKBA),
based on the weight of the composition.

10. The method according to claim 1, wherein the extracts of *Terminalia chebula, Curcuma longa* and *Boswellia serrata* are aqueous, alcoholic or hydroalcoholic extracts.

11. The method according to claim 1, wherein the composition is administered to the patient orally, topically, transdermally, or parenterally.

12. A method for treating a joint disease in a patient in need thereof, wherein the joint disease is selected from the group consisting of rheumatoid arthritis, psoriatic arthritis, osteoarthritis, refractory rheumatoid arthritis, chronic non-rheumatoid arthritis, osteoporosis/bone resorption, collagen degradation, gouty arthritis, lupus, juvenile arthritis, joint pain, or a combination thereof, wherein the method comprises administering to the patient an effective amount of an herbal composition, wherein the herbal composition comprises:
from 20% by weight to 75% by weight of an extract of *Terminalia chebula*;
from 10% by weight to 40% by weight of an extract of *Curcuma longa*; and
from 10% by weight to 40% by weight of a non-acidic, water-immiscible organic solvent extract of a *Boswellia serrata* resin,
based on the total weight of the *Terminalia chebula, Curcuma longa*, and *Boswellia serrata* extracts.

13. The method according to claim 12, wherein the herbal composition comprises:
from 20% by weight to 75% by weight of the extract of *Terminalia chebula*;
from 15% by weight to 40% by weight of the extract of *Curcuma longa*; and
from 10% by weight to 40% by weight of the non-acidic, water-immiscible organic solvent extract of the *Boswellia serrata* resin; and
from 0% by weight to 20% by weight of a *Boswellia serrata* extract which contains at least 5% 3-O-acetyl-11-keto-β-boswellic acid (AKBA),
based on the total weight of the *Terminalia chebula, Curcuma longa*, and *Boswellia serrata* extracts.

14. A method for treating a patient having an inflammation, arthritis, or a joint disease, comprising administering to the patient an effective amount of an herbal composition, wherein the herbal composition comprises:
a therapeutically effective amount of an extract of *Terminalia chebula*;
a therapeutically effective amount of an extract of *Curcuma longa*; and
a therapeutically effective amount of a non-acidic, water-immiscible organic solvent extract of a *Boswellia serrata* resin.

15. A method according to claim 14, wherein the herbal composition is administered to a patient having a joint disease, wherein the joint disease is selected from the group consisting of rheumatoid arthritis, psoriatic arthritis, osteoarthritis, refractory rheumatoid arthritis, chronic non-rheumatoid arthritis, osteoporosis/bone resorption, collagen degradation, gouty arthritis, lupus, juvenile arthritis, joint pain, and a combination thereof.

16. The method according to claim 15, wherein the herbal composition further comprises from 0% by weight to 20% by weight of a *Boswellia serrata* extract which contains at least 5% 3-O-acetyl-11-keto-β-boswellic acid (AKBA), based on the total weight of the *Terminalia chebula, Curcuma longa*, and *Boswellia serrata* extracts.

* * * * *